(12) United States Patent
Erman et al.

(10) Patent No.: US 7,960,580 B2
(45) Date of Patent: Jun. 14, 2011

(54) PROCESS FOR MAKING MENTHYL GLUTARATE

(75) Inventors: Mark B. Erman, Atlantic Beach, FL (US); Joe W. Snow, Kingsland, GA (US)

(73) Assignee: Renessenz, LLC, Jacksonville, FL (US)

( * ) Notice: Subject to any disclaimer, the term of this patent is extended or adjusted under 35 U.S.C. 154(b) by 141 days.

(21) Appl. No.: 12/386,712

(22) Filed: Apr. 22, 2009

(65) Prior Publication Data

US 2010/0274044 A1    Oct. 28, 2010

(51) Int. Cl.
C07C 69/74    (2006.01)
(52) U.S. Cl. ..................................... 560/193
(58) Field of Classification Search ............. None
See application file for complete search history.

(56) References Cited

U.S. PATENT DOCUMENTS

| 3,111,127 | A | * | 11/1963 | Jarboe | ............... 131/276 |
| 7,247,743 | B1 | | 7/2007 | Erman et al. | |
| 2007/0248717 | A1 | | 10/2007 | Johnson et al. | |

OTHER PUBLICATIONS

Hiserodt et al., "Identification of Monomenthyl Succinate, Monomenthyl Glutarate, and Dimenthyl Glutarate in Nature by High Performance Liquid Chromatography-Tandem Mass Spectrometry," *J. Agric. Food Chem. 52.* (2004) 3536.
Hilditch, "The effect of Contiguous Unsaturated Groups on Optical Activity. Part III. The Normal Series of Fatty Dibasic Acids," *J. Chem. Soc.*, (1909) 1578.
Paris, et al.,"Glutaric Acid and Glutarimide,"*Organic Synthesis*, Coll. vol. 4, (1963) 496.
Dewis, "Molecules of Taste and Sensation,"*Chemistry and Technology of Flavours and Fragrances*, D. Rowe, ed., CRC Press, Boca Raton (2005) Ch. 9, pp. 199-243.

* cited by examiner

*Primary Examiner* — Paul A Zucker
(74) *Attorney, Agent, or Firm* — Novak Druce + Quigg LLP

(57) ABSTRACT

A process for making menthyl glutarate is disclosed. The process comprises reacting excess glutaric acid and menthol to produce a mixture comprising monomenthyl glutarate (MMG) and dimenthyl glutarate (DMG), wherein the weight ratio of glutaric acid to menthol is from 1.0 to 1.6 and the resulting mixture comprises from 60 to 70 wt. % of MMG and from 30 to 40 wt. % of DMG.

7 Claims, No Drawings

PROCESS FOR MAKING MENTHYL GLUTARATE

FIELD OF THE INVENTION

The invention relates to a process for making menthyl glutarate useful as a physiological coolant, particularly specific mixtures of monomenthyl glutarate and dimenthyl glutarate.

BACKGROUND OF THE INVENTION

"Menthyl glutarate" or "l-menthyl glutarate" usually refers to the monomenthyl ester of glutaric acid (monomenthyl glutarate or "MMG"), dimenthyl glutarate ("DMG"), and mixtures thereof. Menthyl glutarate is used as a physiological cooling agent in consumer products such as confectionary and oral care (see, for example, U.S. Pat. Appl. Publ. 2007/0248717). According to Hiserodt et al. (*J. Agric. Food Chem.* 52 (2004) 3536), both MMG and DMG are found in nature.

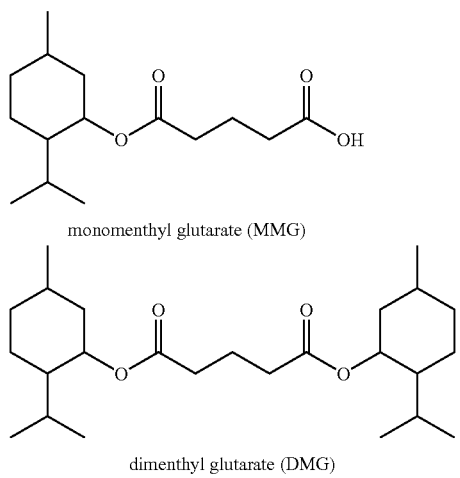

monomenthyl glutarate (MMG)

dimenthyl glutarate (DMG)

Erman et al. disclosed an efficient process for making mixtures of MMG and DMG significantly enriched in the first component (see U.S. Pat. No. 7,247,743). Reaction of menthol with glutaric anhydride in the presence of alkali metal salt catalysts affords mixtures with MMG/DMG ratios ranging from 10 to 20, while a non-catalyzed process produces ratios from 5 to 7.

Hilditch reported a method of preparing pure DMG (*J. Chem. Soc.* (1909) 1578). This method consists of converting glutaric acid into its chloroanhydride, followed by a reaction of the chloroanhydride with excess menthol.

Marketable menthyl glutarate typically contains 60-70% of MMG and 30-40% of DMG, with a total of MMG+DMG≧97% (see Dewis, "Molecules of Taste and Sensation" in *Chemistry and Technology of Flavours and Fragrances*, D. Rowe, ed., CRC Press, Boca Raton (2005) Ch. 9, pp. 199-243). However, an efficient process for obtaining such mixtures has not been described in the literature. Of course, MMG and DMG can be obtained separately by the above-mentioned methods and blended in the desired proportion, but this approach is costly. A more economical way to obtain commercially desirable mixtures of MMG and DMG, preferably one that avoids the need for the relatively expensive glutaric anhydride, is still needed.

SUMMARY OF THE INVENTION

The invention relates to a process for making menthyl glutarate. The process comprises reacting glutaric acid and menthol to produce a mixture comprising monomenthyl glutarate and dimenthyl glutarate, wherein the weight ratio of glutaric acid to menthol is from 1.0 to 1.6 and the resulting mixture comprises from 60 to 70 wt. % of MMG and from 30 to 40 wt. % of DMG. Although our calculations predicted otherwise, we surprisingly found that excess glutaric acid provides menthyl glutarate that contains a commercially desirable proportion of MMG to DMG.

DETAILED DESCRIPTION OF THE INVENTION

"Menthyl glutarate" as used herein refers to monomenthyl glutarate (MMG), dimenthyl glutarate (DMG), and their mixtures. In the inventive process, particular mixtures of MMG and DMG are produced by reacting excess glutaric acid with menthol.

Suitable menthol includes all possible stereoisomers and isomer mixtures, including any combination of the eight possible stereoisomers of menthol. Thus, suitable menthol includes, for example, l-menthol, d-menthol, dl-menthol (i.e., a racemic mixture of l-menthol and d-menthol), isomers of neomenthol, isomenthol, or neoisomenthol, or mixtures thereof. Because it provides menthyl glutarate having excellent physiological cooling properties, l-menthol is particularly preferred. The purity level of the menthol is generally not considered critical.

Glutaric acid suitable for use can be obtained commercially. It can also be synthesized by many routes starting from, for instance, γ-butyrolactone, dihydropyran, cyclopentene, glutaraldehyde, or other raw materials (see *Organic Syntheses. Coll. Vol.* 4, (1963) 496 and references cited therein). The purity level of the glutaric acid is generally not considered critical.

Menthol and glutaric acid are reacted under conditions effective to produce a mixture comprising 60 to 70 wt. % of monomenthyl glutarate and 30 to 40 wt. % of dimenthyl glutarate. Such mixtures are marketed commercially, but they are difficult to make directly by known methods. Normally, the components (MMG, DMG) are made separately and then combined in the desired proportion. Surprisingly, we found that conditions valuable for making product mixtures having 60-70 wt. % MMG and 30-40 wt. % DMG utilize an excess of glutaric acid.

The target mixtures have weight ratios (MMG/DMG) ranging from 1.500 (60:40 weight ratio) to 2.333 (70:30 weight ratio), with a midpoint at 1.857 (65:35 weight ratio). These correspond to molar ratios ranging from 2.267 to 3.526 (midpoint: 2.807). Each molecule of MMG or DMG binds one molecule of glutaric acid. MMG binds one molecule of menthol, but DMG binds two molecules of menthol. A simple calculation shows that the molar midpoint ratio for MMG/DMG of 2.807 corresponds to a molar ratio of the bound glutaric acid/menthol (GA/M) of 0.792, or a weight ratio GA/M=0.670:

Thus, the moles of glutaric acid (GA) in the midpoint formulation are given by:

$$\begin{array}{r} 2.807 \text{ moles} \times 1 \text{ mole } GA/\text{mole } MMG \\ +1.000 \text{ mole} \times 1 \text{ mole } GA/\text{mole } DMG \\ \hline 3.807 \text{ moles glutaric acid} \end{array}$$

For moles of menthol (M) in the midpoint formulation:

$$2.807 \text{ moles} \times 1 \text{ mole } M/\text{mole } MMG$$
$$+1.000 \text{ mole} \times 2 \text{ moles } M/\text{mole } DMG$$
$$\overline{4.807 \text{ moles menthol}}$$

Mole ratio GA/M=3.807/4.807=0.792
Weight ratio GA/M=0.792×(132.11 g/mole GA/156.27 g/mole M)=0.670.

Using similar calculations, the borderline molar ratios for MMG/DMG of 2.267 and 3.526 give, respectively, molar ratios of GA/M=0.766 and 0.819 and corresponding weight ratios of GA/M=0.648 and 0.692.

Based on these calculations, we predicted that esterification of glutaric acid with excess menthol in a weight ratio GA/M within this range (0.648 to 0.692), especially at the midpoint (0.670), would provide a product with an MMG/DMG weight ratio within the desired range of 1.500 to 2.333.

Our experiments, however, showed that at the calculated midpoint GA/M ratio, the final product contained MMG and DMG in a weight ratio 0.62, i.e., well outside the target range (see Table 1, Comparative Example 1).

Surprisingly, we found that the desired ratio MMG/DMG is obtained by direct esterification of glutaric acid with menthol when glutaric acid is used in excess. The best results—with the MMG/DMG ratios within the desired range of 1.500-2.333—are obtained with GA/M ratios respectively from about 1.05 to about 1.56, i.e., far from the calculated weight ratios for GA/M of 0.648 to 0.692. The results closest to the desired midpoint ratio MMG/DMG are obtained with starting material ratios GA/M from 1.17 to 1.40 (see Table 1).

The inventive process is simple to practice using conventional equipment and techniques. Menthol and excess glutaric acid are reacted under conditions effective to produce a mixture comprising monomenthyl glutarate and dimenthyl glutarate. The initial weight ratio of glutaric acid to menthol is adjusted to range from 1.0 to 1.6, preferably from 1.05 to 1.56. This provides a product mixture that comprises from 60 to 70 wt. % of MMG and from 30 to 40 wt. % of DMG.

In one convenient approach, the menthol and glutaric acid are combined and heated in the presence of a solvent capable of forming an azeotrope with water. The water generated as the reaction proceeds is then easily removed from the reaction mixture using a Barrett trap or similar device. Typically, the reaction is allowed to proceed until most of the menthol has been consumed, as can be conveniently measured using gas chromatography or other suitable techniques. Preferred solvents are $C_5$-$C_8$ aliphatic hydrocarbons, $C_6$-$C_9$ aromatic hydrocarbons, and mixtures thereof. Examples include pentane, hexanes, heptanes, octanes, benzene, toluene, xylenes, ethylbenzene, and the like, and mixtures thereof.

Because glutaric acid is used in excess, it is preferred to recover the unreacted portion for reuse. This can be accomplished by any desired methodology. In one approach, the product mixture, following removal of the water of reaction, is diluted with additional hydrocarbon solvent. Glutaric acid crystallizes or precipitates, and is recovered by filtration, decantation, centrifugation, or the like. Alternatively, the excess glutaric acid is removed from the product mixture by water extraction and is recovered from the aqueous phase. The recovered glutaric acid is preferably used alone or in combination with fresh glutaric acid as a starting material in another reaction with menthol to make menthyl glutarate.

After removal of the glutaric acid, the menthyl glutarate product is typically stripped to remove the remaining solvent and traces of menthol. Menthyl glutarate produced by the process of the invention is valuable for many traditional applications for physiological cooling agents, including, for example, comestible items such as chewing gum, chewing tobacco, cigarettes, ice cream, confectionary and drinks, as well as in toiletries and pharmaceutical or cosmetic preparations such as dentifrices, mouthwashes, perfumes, powders, lotions, ointments, oils, creams, sunscreens, shaving creams and aftershaves, shower gels or shampoos.

The following examples merely illustrate the invention. Those skilled in the art will recognize many variations that are within the spirit of the invention and scope of the claims.

Examples 4-13 and Comparative Examples 1-3 and 14

Reaction of Menthol and Glutaric Acid: General Procedure

A mixture of menthol (156.3 g), glutaric acid (amount given in Table 1), and heptane (75 g) is heated to reflux, and the water formed is collected and periodically removed using a Barrett trap. The reaction continues until gas chromatography (GC) analysis shows that the concentration of menthol has dropped below 8-10%. The mixture is allowed to cool to ambient temperature and is diluted with additional heptane (about 35 g). Excess glutaric acid crystallizes and is removed by filtration. The menthyl glutarate product, which is now practically free of unreacted glutaric acid, is heated under vacuum to remove heptane and unreacted menthol (the residual concentration of menthol should not exceed 0.8%), and the final product is analyzed by GC. The results are given in Table 1.

TABLE 1

Esterification of l-Menthol with Glutaric acid

| Ex. | GA charged, g | Weight ratio GA/M | Menthol, % | MMG, % | DMG, % | Weight Ratio MMG/DMG |
|---|---|---|---|---|---|---|
| C1* | 104.6 | 0.669 | 0.7 | 37.8 | 60.6 | 0.62 |
| C2* | 134.6 | 0.861 | 0.7 | 52.1 | 46.6 | 1.12 |
| C3* | 154.6 | 0.989 | 0.7 | 57.5 | 40.8 | 1.41 |
| 4 | 164.6 | 1.053 | 0.6 | 59.5 | 39.3 | 1.52 |
| 5 | 174.6 | 1.117 | 0.3 | 60.6 | 38.4 | 1.58 |
| 6 | 183.5 | 1.174 | 0.3 | 61.2 | 38.0 | 1.61 |
| 7 | 193.5 | 1.238 | 0.3 | 63.4 | 35.7 | 1.78 |
| 8 | 198.5 | 1.270 | 0.2 | 64.6 | 34.7 | 1.86 |
| 9 | 203.5 | 1.302 | 0.4 | 65.0 | 34.0 | 1.91 |
| 10 | 213.5 | 1.366 | 0.6 | 67.1 | 31.9 | 2.11 |
| 11 | 223.5 | 1.430 | 0.3 | 68.2 | 31.0 | 2.20 |
| 12 | 233.5 | 1.494 | 0.2 | 68.7 | 30.7 | 2.24 |
| 13 | 243.5 | 1.558 | 0.3 | 69.3 | 30.0 | 2.31 |
| C14* | 253.5 | 1.622 | 0.4 | 70.5 | 28.6 | 2.47 |

*Comparative examples.
GA = glutaric acid,
M = menthol,
MMG = monomenthyl glutarate,
DMG = dimenthyl glutarate.
All examples start with 156.3 g of l-menthol and the amount of glutaric acid indicated in the table.

The examples are meant only as illustrations. The following claims define the invention.

We claim:

1. A process which comprises reacting menthol and glutaric acid to produce a mixture comprising monomenthyl glutarate (MMG) and dimenthyl glutarate (DMG), wherein the weight ratio of glutaric acid to menthol is from 1.0 to 1.6 and the resulting mixture comprises from 60 to 70 wt. % of MMG and from 30 to 40 wt. % of DMG.

2. The process of claim 1 wherein the reaction is performed under reflux in the presence of a solvent that forms an azeotrope with water.

3. The process of claim 2 wherein the solvent is selected from the group consisting of $C_5$-$C_8$ aliphatic hydrocarbons, $C_6$-$C_9$ aromatic hydrocarbons, and mixtures thereof.

4. The process of claim 1 wherein upon completion of the reaction unreacted glutaric acid is recovered and reused in another reaction with menthol.

5. The process of claim 4 wherein the unreacted glutaric acid is recovered by crystallization or aqueous extraction.

6. The process of claim 1 wherein the weight ratio of glutaric acid to menthol is from 1.05 to 1.56.

7. The process of claim 1 wherein the weight ratio of glutaric acid to menthol is from 1.17 to 1.40.

* * * * *